United States Patent
Kitagawa et al.

(10) Patent No.: US 7,495,099 B2
(45) Date of Patent: Feb. 24, 2009

(54) HIGH-MOLECULAR WEIGHT DERIVATIVES OF CAMPTOTHECINS

(75) Inventors: Masayuki Kitagawa, Kitakatsushika-gun (JP); Kazuya Okamoto, Adachi-ku (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 574 days.

(21) Appl. No.: 10/532,670

(22) PCT Filed: Oct. 29, 2003

(86) PCT No.: PCT/JP03/13838

§ 371 (c)(1),
(2), (4) Date: Jun. 16, 2005

(87) PCT Pub. No.: WO2004/039869

PCT Pub. Date: May 13, 2004

(65) Prior Publication Data

US 2006/0067910 A1    Mar. 30, 2006

(30) Foreign Application Priority Data

Oct. 31, 2002    (JP) .............................. 2002-316942

(51) Int. Cl.
*C07D 491/22* (2006.01)
*A61K 31/4745* (2006.01)
(52) U.S. Cl. .............................. 546/48; 514/283; 546/14
(58) Field of Classification Search ................ 514/283; 546/48, 14
See application file for complete search history.

(56) References Cited

U.S. PATENT DOCUMENTS

| 6,410,731 | B2 | 6/2002 | Currant et al. ................ 546/41 |
| 2001/0003779 | A1 | 6/2001 | Curran et al. ................ 546/41 |

FOREIGN PATENT DOCUMENTS

| EP | 0 757 049 | 2/1997 |
| JP | 5-117385 | 5/1993 |
| JP | 6-206832 | 7/1994 |
| JP | 2003-342167 | 12/2003 |
| JP | 2003-342168 | 12/2003 |
| WO | 99/53951 | 10/1999 |
| WO | 01/92584 | 12/2001 |
| WO | 03/000771 | 1/2003 |

OTHER PUBLICATIONS

A.V. Shur, "High-molecular weight compounds", Course for Universities, Third Edition, revised and supplemented, "Visshaja shkola" Publishing House, 1981, 656 page.
Russia communication dated Apr. 20, 2007, together with an English translation.
The European communication dated Sep. 25, 2008.

*Primary Examiner*—Charanjit S Aulakh
(74) *Attorney, Agent, or Firm*—Nields & Lemack

(57) ABSTRACT

It is intended to provide water-soluble derivative of camptothecins which are excellent in therapeutic effect and suitable for chemotherapy for cancer. Namely, a water-soluble high-molecular weight derivative of camptothencins being excellent in sustained-release which is obtained by ester-bonding a carboxylic acid group of a polyethylene glycol-polycarboxylic acid polymer to a phenolic hydroxyl group of phenolic camptothencins.

6 Claims, 2 Drawing Sheets

HIGH-MOLECULAR WEIGHT DERIVATIVES OF CAMPTOTHECINS

TECHNICAL FIELD

The present invention relates to a high-molecular weight derivative of camptothecins, and a method of producing the same and a use thereof.

BACKGROUND TECHNOLOGY

Camptothecin is an antitumor alkaloid contained in plants such as *Camptotheca acuminata* of Chinese origin, and has an extremely poor solubility in water, therefore, clinically usable water-soluble derivatives thereof have been studied. Further, it is known that introduction of a substituent such as a hydroxyl group, alkoxyl group, amino group and the like onto the benzene ring reinforces its effect (Non-patent Literature 1).

For example, Patent Literature 1 and Patent Literature 2 refer to a high-molecular weight derivative of camptothecin carrying bonded polyethylene glycol as a prodrug. These patents report optimization of the molecular weight of the polyethylene glycol portion, and simultaneously, also the importance of a spacer bonding the polyethylene glycol portion to camptothecin. It is desirable that the spacer is stably present during residence of the above-mentioned derivative in an organism and is cut quickly only at a target region. These literatures judge that a mere ester type bonded compound of alcohol shows slow hydrolysis rate at a target region and sufficient drug concentration cannot be obtained, and disclose spacers which are easily hydrolyzed at a target region.

As a water-soluble derivative of camptothecin, CPT-11 (7-ethyl-10-piperidinopiperidinocarbonyloxycamptothecin) is known (Non-patent Literature 1).

Further, Patent Literature 3 describes a high-molecular weight derivative of camptothecins which carries bonded polyglutamic acid.

On the other hand, Patent Literature 4 and Non-patent Literature 2 show that an aggregate of molecules obtained by bonding a drug to a block copolymer of polyethylene glycol and polyaspartic acid can form micelle thereby enhancing its water-solubility and increase the drug content per polymer molecule, Patent Literature 5 shows a polymer anticancer agent obtained by bonding an anticancer substance to a side chain carboxylic acid of a block copolymer of polyethylene glycol and polyglutamic acid, and Patent Literature 6 shows a polymer drug carrier obtained by bonding a hydrophobic substance to a side chain carboxylic acid of a block copolymer of polyethylene glycol and acidic amino acid polymer. However, Patent Literature 4, Patent Literature 5 and Patent Literature 6 do not describe a bonded compound of camptothecins.

LIST OF LITERATURES

Patent Literature 1: Japanese Patent Application Laying Open (KOHYO) No. 10-513187

Patent Literature 2: Japanese Patent Application Laying Open (KOHYO) No. 2000-517304

Patent Literature 3: International Publication No. WO01/70275 pamphlet

Patent Literature 4: Japanese Patent No. 2694923

Patent Literature 5: Japanese Patent Application Laying Open (KOKAI) No. 5-955

Patent Literature 6: Japanese Patent No. 3268913

Non-patent Literature 1: S. Miyasaka et al, Anticancer Agent Irinotecan, Gendai Kagaku, October 1999 issue, Tokyo Kagaku Dozin, pp. 58 to 66

Non-patent Literature 2: T. Nakanishi et al., Development of the polymer micelle carrier system for doxorubicin, Journal of Controlled Release, 2001, 74, Elsevier, pp. 295 to 302

Prodrugs carrying polyethylene glycol bonded described in Patent Literature 1 and Patent Literature 2 can bond only 1 to 2 drugs per polyethylene glycol molecule because of its structure, and therefore, for the dosing of effective amount of drugs, a large amount of polymers should be administered.

CPT-11 which is a water-soluble derivative of camptothecin manifests serious side effects and is not a easy-to-use drug, consequently, there is a desire for novel camptothecin derivatives.

In adriamycin bonded compounds described specifically in Patent Literature 4, Patent Literature 5 and Non-patent Literature 2, a block copolymer and an adriamycin residue are bonded by an amide bond which is a chemically stable bonding mode, and actually, as described in Non-patent Literature 2, adriamycin bonded does not have antitumor activity.

DISCLOSURE OF INVENTION

The present inventors have made an intensive effort to solve the problems as described above, and as a result found a high-molecular weight derivative of camptothecins obtained by bonding a carboxylic acid group of a copolymer of polyethylene glycol and a polymer having a side chain carboxylic acid group, to phenolic camptothecins through a phenylester structure, leading to the present invention.

Namely, the present invention relates to (1) A high-molecular weight derivative of camptothecins having a structure wherein a carboxylic acid group of a copolymer of polyethylene glycol and a polymer having a carboxylic acid group at the side chain, is combined with a phenolic hydroxyl group of phenolic camptothecins via an ester bond;

(2) The high-molecular weight derivative of camptothecins according to (1), wherein the copolymer of polyethylene glycol and a polymer having a carboxylic acid group at the side chain is a block copolymer of polyethylene glycol and a polymer having a carboxylic acid group at the side chain;

(3) The high-molecular weight derivative of camptothecins according to (1) or (2), wherein the polymer having a carboxylic acid group at the side chain is an acidic amino acid polymer.

(4) The high-molecular weight derivative of camptothecins according to (3), wherein the acidic amino acid polymer is a polyglutamic acid or a polyaspartic acid.

(5) A high-molecular weight derivative of camptothecins of the general formula (I):

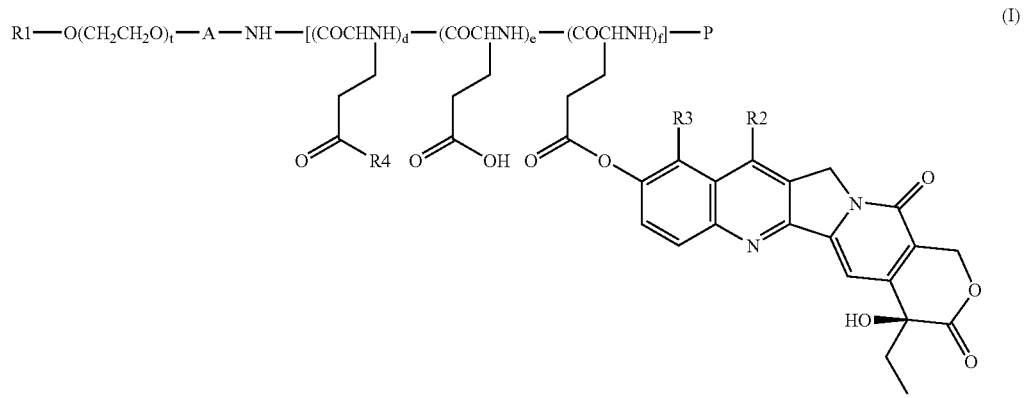

[wherein, R1 represents a hydrogen atom or a (C1 to C6) alkyl group optionally having a substituent, t represents an integer of 5 to 11500, A represents a bonding group, d+e+f represents an integer of 3 to 200, R2 represents a hydrogen atom or a (C1 to C6) alkyl group optionally having a substituent or a silyl group optionally having a substituent, R3 represents a hydrogen atom or a (C1 to C6) alkyl group optionally having a substituent, R4 may be the same or different and represents a (C1 to C20) alkoxyl group optionally having a substituent, a (C1 to C20) alkylamino group optionally having a substituent, a di(C1 to C20) alkylamino group optionally having a substituent or a (C1 to C20) alkylaminocarbonyl (C1 to C20) alkylamino group optionally having a substituent, and P represents a hydrogen atom, a (C1 to C6) acyl group or a (C1 to C6) alkoxycarbonyl group;

(6) The high-molecular weight derivative of camptothecins according to (5), wherein R1 is a (C1 to C4) alkyl group optionally having a substituent, t is an integer of 100 to 300, A is a (C2 to C6) alkylene group, d+e+f is an integer of 6 to 60, the ratio of d is 0 to 60%, the ratio of e is 0 to 60% and the ratio of f is 1 to 100% based on d+e+f, R2 is a hydrogen atom or a (C1 to C4) alkyl group optionally having a substituent, R3 is a hydrogen atom or a (C1 to C4) alkyl group having no substituent, R4 may be the same or different and is a (C1 to C8) alkoxyl group optionally having a substituent, a (C1 to C8) alkylamino group optionally having a substituent, a di (C1 to C8) alkylamino group optionally having a substituent or a (C1 to C8) alkylaminocarbonyl (C1 to C8) alkylamino group optionally having a substituent, and P is a (C2 to C4) acyl group;

(7) The high-molecular weight derivative of camptothecins according to (6), wherein R1 is a methyl group, A is a trimethylene group, R2 is a hydrogen atom, R3 is a dimethylaminomethyl group, R4 is an isopropylaminocarbonylisopropylamino group, and P is an acetyl group.

(8) The high-molecular weight derivative of camptothecins according to (6), wherein R1 is a methyl group, A is a trimethylene group, R2 is an ethyl group, R3 is a hydrogen atom, R4 is an isopropylaminocarbonylisopropylamino group, and P is an acetyl group.

(9) A high-molecular weight derivative of camptothecins, obtained by reacting a block copolymer of a polyethylene glycol portion and polyaminoglutamic acid or polyaspartic acid, with a phenolic camptothecin in an organic solvent using a condensing agent.

(10) A method of producing the high-molecular weight derivative of camptothecins according to any of (1) to (8), comprising combining a carboxylic acid group of a copolymer of polyethylene glycol and a polymer having a carboxylic acid group at the side chain, with a phenolic hydroxyl group of phenolic camptothecins via an ester bond, using a condensing agent.

(11) An anticancer agent comprising the high-molecular weight derivative of camptothecins according to any of (1) to (9).

BEST MODE FOR CARRYING OUT THE INVENTION

Figure 1:
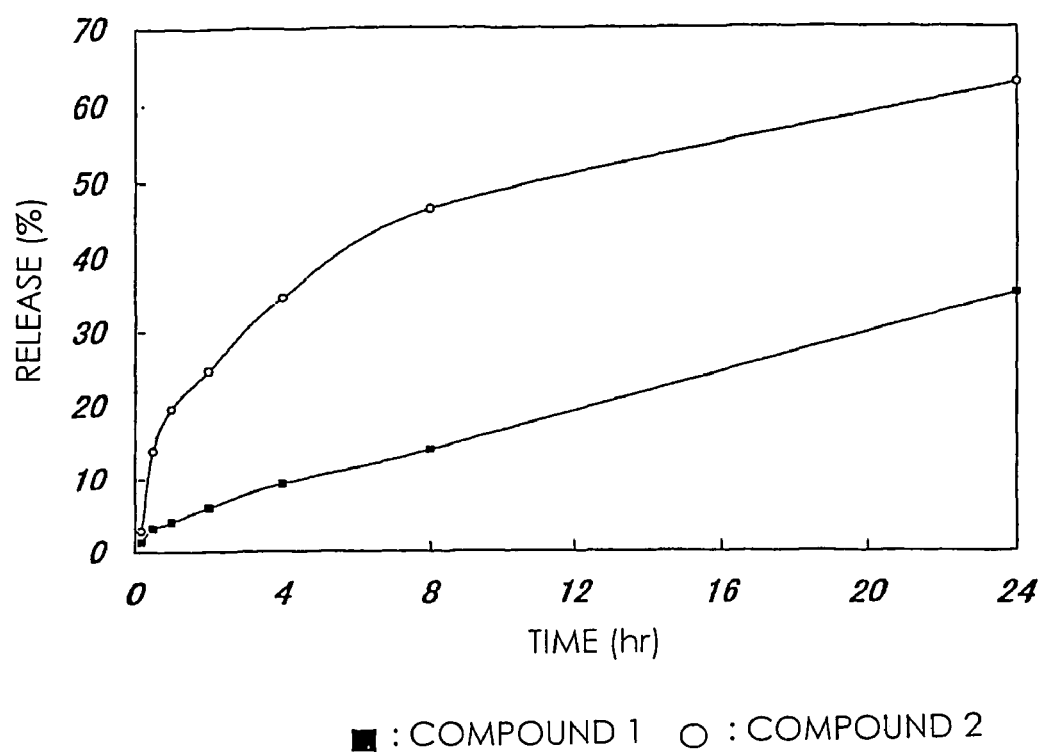
FIG. 1 is a curve diagram showing the release amount of drugs in the absence of a hydrolytic enzyme in terms of ratio based on the total drug amount in Example 3. The abscissa represents time and the ordinate represents release amount.

The high-molecular weight derivative of camptothecins of the present invention is characterized in that it has a structure wherein a phenolic hydroxyl group of phenolic camptothecins is combined with a carboxylic acid group of a polymer having a carboxylic acid group at the side chain and polyethylene glycol portion via a phenylester bond.

In the present invention, phenolic camptothecins mean a camptothecin derivative having a phenolic hydroxyl group, and are not particularly restricted. The above-mentioned phenolic hydroxyl group can be bonded to aromatic ring portions in a camptothecin skeleton, particularly, to any of 1 to 4 positions selected from 9-position, 10-position, 11-position and 12-position thereof. Specific examples of the above-mentioned phenolic camptothecins include 7-ethyl-10-hydroxycamptothecin, topotecan (9-dimethylaminomethyl-10-hydroxycamptothecin; manufactured by Glaxo Smith-Kline K.K.) and the like.

The copolymer of polyethylene glycol and a polymer having a carboxylic acid group at the side chain in the present invention includes graft polymers, block polymers and the like.

As the graft polymers are mentioned the polymers obtained by subjecting a condensate of polyethylene glycol and acrylic acids, and acrylic acids or maleic anhydride and the like to a copolymerization reaction, and if necessary, to a hydrolysis reaction, and the like, described, for example, in Japanese Patent Application Laying Open (KOKAI) No. 11-279083. As the block polymers are mentioned the polymers obtained by bonding polyethylene glycol having a functional group at the end and polycarboxylic acids having a functional group at the end, and the polymers obtained by a polymerization reaction of an amino acid activated compound which initiates polymerization with polyethylene glycol having an amino group at the end described in Patent Literature 5.

The polyethylene glycol in the present invention include also polyethylene glycol having both ends modified or one end modified, and modification groups at both ends may be the same or different. The modification group at the end includes a (C1 to C6) alkyl groups optionally having a substituent. The (C1 to C6) alkyl group optionally having a substituent includes preferably (C1 to C4) alkyl groups optionally having a substituent, and specific examples thereof include methyl group, ethyl group, n-propyl group, i-propyl group, n-butyl group, s-butyl group, t-butyl group, benzyl group, dimethoxyethyl group, diethoxyethyl group and the like.

The molecular weight of polyethylene glycol portion is usually approximately 300 to 500000, preferably approximately 500 to 100000, further preferably approximately 1000 to 50000.

The number of carboxylic acid groups per one molecule of the copolymer of polyethylene glycol and a polymer having a carboxylic acid group at the side chain is preferably 3 to 200, more preferably 6 to 60. The number of carboxylic acid groups is determined by neutralization titration with an alkali. In this procedure, when a substituent such as camptothecins and the like is bonded to a carboxylic acid group, the number may be measured after hydrolysis.

The molecular weight of the copolymer of polyethylene glycol and a polymer having a carboxylic acid group at the side chain in the present invention is usually approximately 500 to 500000, preferably approximately 600 to 100000, further preferably 800 to 80000.

The molecular weight in this specification means weight-average molecular weight measured by a GPC method.

In the present invention, the bonding amount of camptothecins to be bonded to a copolymer of polyethylene glycol and a polymer having a carboxylic acid group at the side chain, is not particularly restricted provided that it is an amount showing drug effect, and usually, it is 1 to 100%, preferably 10 to 90% of the total carboxylic acid group number of the polymer.

The high-molecular weight derivative of camptothecins of the present invention includes also derivatives showing an effect as a prodrug.

As the copolymer of polyethylene glycol and a polymer having a carboxylic acid group at the side chain in the present invention, block copolymers are preferably mentioned, and further preferable are block copolymers of acidic amino acid polymers and polyethylene glycol. The polymer having a carboxylic acid group at the side chain includes, for example, polyacrylic acid, polymethacrylic acid, polymalic acid, polyaspartic acid, polyglutamic acid and the like, and preferable are polyaspartic acid, polyglutamic acid and the like.

Examples of the block copolymer of a polymer having a carboxylic acid group at the side chain and polyethylene glycol in the present invention include alkoxypolyethylene glycol-polyacrylic acid, alkoxypolyethylene glycol-polymethacrylic acid, alkoxypolyethylene glycol-polyglutamic acid, alkoxypolyethylene glycol-polyaspartic acid and the like. Preferable examples of the block copolymer include (C1 to C4) alkoxypolyethylene glycol-polyaspartic acids or (C1 to C4) alkoxypolyethylene glycol-polyglutamic acids and the like.

Further, as the high-molecular weight derivative of camptothecins which bonded to a block copolymer of polyethylene glycol and an acidic amino acid polymer by phenolic camptothecins in the present invention include, for example, compounds of the above-mentioned general formula (I) [wherein, R1 represents a hydrogen atom or a (C1 to C6) alkyl group optionally having a substituent, t represents an integer of 5 to 11500, A represents a bonding group, d+e+f represents an integer of 3 to 200, R2 represents a hydrogen atom, a (C1 to C6) alkyl group optionally having a substituent or a silyl group optionally having a substituent, R3 represents a hydrogen atom or a (C1 to C6) alkyl group optionally having a substituent, R4 may be the same or different and represents a (C1 to C20) alkoxyl group optionally having a substituent, a (C1 to C20) alkylamino group optionally having a substituent, a di (C1 to C20) alkylamino group optionally having a substituent or a (C1 to C20) alkylaminocarbonyl (C1 to C20) alkylamino group optionally having a substituent, and P represents a hydrogen atom, a (C1 to C6) acyl group or (C1 to C6) alkoxycarbonyl group].

As the (C1 to C6) alkyl group optionally having a substituent represented by R1 in the general formula (I), mentioned are straight chain or branched (C1 to C6) alkyl groups optionally having a substituent, and preferable are straight chain or branched (C1 to C4) alkyl groups optionally having a substituent, and specific examples thereof include methyl group, ethyl group, n-propyl group, i-propyl group, n-butyl group, t-butyl group, benzyl group, 2,2-dimethoxyethyl group, 2,2-diethoxyethyl group and the like and methyl group is particularly preferable.

The bonding group represented by A in the general formula (I) is a bonding portion of polyethylene glycol and an acidic amino acid polymer, and is not particularly restricted provided that it does not disturb physiological activity, and preferable are (C2 to C6) alkylene groups, and specific examples thereof include ethylene group, trimethylene group, butylene group and the like, and trimethylene group is particularly preferable.

Alkyl groups of the (C1 to C6) alkyl group optionally having a substituent represented by R2 in the general formula (I) include straight chain or branched (C1 to C6) alkyl groups, and preferable are straight chain or branched (C1 to C4) alkyl groups, and specific examples thereof include methyl group, ethyl group, n-propyl group, i-propyl group, n-butyl group, t-butyl group and the like. The substituent includes an amino group, (C1 to C3) alkylamino groups, di(C1 to C3) alkylamino groups and the like.

The silyl group optionally having a substituent represented by R2 in the general formula (I) includes, for example, (1,1-dimethylethyl)dimethylsilyl group and the like.

R2 in the general formula (I) includes, specifically, a hydrogen atom, methyl group, ethyl group, dimethylaminomethyl group, 2-[(1-methylethyl)amino]ethyl group, 2-(trimethylsilyl)ethyl group, (4-methyl-1-piperidinyl)methyl group, [(2,3-dideoxy-α-D-erythrohexy-2-enopiranosyl)oxy]methyl group and the like. R2 is preferably a hydrogen atom or ethyl group.

Alkyl groups of the (C1 to C6) alkyl group optionally having a substituent represented by R3 in the general formula (I) include the same groups as for the (C1 to C6) alkyl group represented by above-mentioned R2. The substituent thereof includes the same substituents as for the (C1 to C6) alkyl group optionally having a substituent represented by above-mentioned R2.

As R3 in the general formula (I) includes, specifically, a hydrogen atom, methyl group, ethyl group, dimethylaminomethyl group, 2-[(1-methylethyl)amino]ethyl group and the like. R3 is preferably a hydrogen atom or dimethylaminomethyl group.

As the (C1 to C20) alkoxyl group optionally having a substituent represented by R4 in the general formula (I), preferably mentioned are (C1 to C8) alkoxyl groups optionally having a substituent, and specific examples thereof include methoxy group, ethoxy group, propoxy group, isopropoxy group, benzyloxy group, phenetyloxy group and the like.

As the (C1 to C20) alkylamino group optionally having a substituent represented by R4 in the general formula (I), preferably mentioned are (C1 to C8) alkylamino groups optionally having a substituent, and specific examples thereof include methylamino group, ethylamino group, propylamino group, isopropylamino group, benzylamino group, acetylamino group and the like. Amino acid groups having a carboxyl group protected may also be permissible.

As the di (C1 to C20) alkylamino group optionally having a substituent represented by R4 in the general formula (I), preferably mentioned are di(C1 to C8) alkylamino groups optionally having a substituent, and specific examples thereof include N,N-dimethylamino group, N,N-diethylamino group, N,N-dipropylamino group, N,N-diisopropylamino group, N,N-dibenzylamino group, N-methyl-N-benzylamino group and the like.

The (C1 to C20) alkylaminocarbonyl (C1 to C20) alkylamino group optionally having a substituent represented by R4 in the general formula (I) is N(R5)CONHR6 [R5 and R6 are (C1 to C20) alkyl groups which may be the same or different], and preferably mentioned are (C1 to C8) alkylaminocarbonyl (C1 to C8) alkylamino groups optionally having a substituent, and specific examples thereof include methylaminocarbonylmethylamino group, ethylaminocarbonylethylamino group, isopropylaminocarbonylisoporopylamino group, cyclohexylaminocarbonylcyclohexylamino group and the like.

The (C1 to C6) acyl group represented by P in the general formula (I) is not particularly restricted, and for example, formyl group, acetyl group, propionyl group, pivaloyl group and the like are mentioned, the acetyl group being preferable.

The (C1 to C6) alkoxycarbonyl group represented by P in the general formula (I) is not particularly restricted, and for example, methoxycarbonyl group, ethoxycarbonyl group, t-butoxycarbonyl group and the like are mentioned.

d, e and f in the general formula (I) are each integer, and d+e+f is an integer of 3 to 200, preferably 6 to 60, further preferably 6 to 40. The ratio of d is preferably 0 to 60%, more preferably 5 to 50%, further preferably 15 to 40%, the ratio of e is preferably 0 to 60%, more preferably 0 to 40%, and the ratio of f is 1 to 100%, preferably 10 to 90%, more preferably 30 to 70%, based on d+e+f. In a compound of the general formula (I), polyglutamic acid to which camptothecins and other groups are bonded and free polyglutamic acid may be of block polymerization type or random polymerization type. d+e+f is the total number of carboxylic acid groups in one molecule of the above-mentioned polymer, and determined by the charge amount of raw materials and the above-mentioned neutralization titration. The number f of glutamic acid groups to which camptothecins are bonded in the polymer can be determined, for example, by the intensity of ultraviolet absorption spectrum. The number d of glutamic acid groups to which R4 is bonded can be determined, when a high-molecular weight derivative of camptothecin forms micelle, by measuring hydrogen nuclear magnetic resonance spectrum under conditions decomposing the micelle, and calculating from the intensity ratio of resulting signals.

t in the general formula (I) is an integer usually of approximately 5 to 11500, preferably approximately 8 to 2300, further preferably approximately 16 to 1200, particularly preferably approximately 100 to 300. The above-mentioned t can be determined, for example, by subtracting the molecular weight of a partial polymer having a carboxylic acid group at the side chain based on the total number of the carboxylic acid groups from the molecular weight of a polymer having polyethylene glycol portion and a carboxylic acid group at the side chain.

The above-mentioned block copolymer of polyethylene glycol and polyglutamc acid to which camptothecins are bonded may form micelle having a shell made of polyethylene glycol in water.

Production of a high-molecular weight derivative of camptothecins of the present invention can be performed, for example, by subjecting a polyethylene glycol-polyglutamic acid block copolymer prepared substantially according to the method described in Patent Literature 5 and, camptothecins having a phenolic hydroxyl group, wherein the active group is protected when an active group possibly causing a side reaction is present, to a reaction in a solvent in which both of them are dissolved, preferably in an organic solvent, more preferably in a water-soluble polar solvent such as N,N-dimethylformamide (DMF), 1,3-dimethyl-2-imidazolidinone (DMI), N-methylpyrrolidone (NMP) and the like, at temperatures usually of 0 to 180° C., preferably 5 to 50° C., using a condensing agent such as dicyclohexylcarbodiimide (DCC), diisopropylcarbodiimide (DIPC), 1-ethyl-3-(3-dimethylaminopropyl)carbodiimide hydrochloride (WSC), 1-ethoxycarbonyl-2-ethoxy-1,2-dihydroxyquinolinone (EEDQ), di-tert-butyl dicarbonate ((BOC)$_2$O) and the like. In the above-mentioned condensation reaction, reaction auxiliaries such as N,N-dimethylaminopyridine (DMAP) and the like may be used. After the reaction, de-protection is conducted if necessary, and usual operations for separation and the like are effected, thus, a high-molecular weight derivative of camptothecins of the present invention can be obtained.

However, the method of producing a high-molecular weight derivative of camptothecins of the present invention is not limited to the above-mentioned method.

The composition of monomers in the high-molecular weight derivatives can be controlled by adjusting reaction conditions. For example, by changing condensing agents, specifically, by an ester activation method using EEDQ or (BOC)$_2$O and the like as a condensing agent, or by an acid chloride formation method using phosphorus oxychloride and the like, the number d of polyglutamic acids to which a group other than camptothecins is bonded in a compound of the general formula (I) can be adjusted to 0. Additionally, a high-molecular weight derivative of camptothecins in which R4 is an alkylaminocarbonylalkylamino group is obtained also by a reaction using the above-mentioned carbodiimides as a condensing agent.

As a method of introducing R4 into a compound of the general formula (I), there are mentioned a method in which a carboxylic acid group of a copolymer is activated by the method as described above, then, alcohol, amine and the like in an amount to be added is reacted under a basic condition, a method in which alcohol and amine are activated previously, then, reacted with a polymer, and the like. Further, after purification of a polymer, un-reacted carboxylic acid groups in a polymer can be re-activated according to the same reaction, and to which, camptothecins having a phenolic hydroxyl group may be condensed. Alternatively, when other alcohols, amines and the like are reacted repeatedly, a mixture of various substituents R4 can be synthesized, therefore, finally, camptothecins having a phenolic hydroxyl group may be condensed.

The high-molecular weight derivative of camptothecins of the present invention can be used as an anticancer agent. It is estimated that the high-molecular weight derivative of camptothecins of the present invention releases camptothecins in a body mainly as a prodrug and this shows antitumor activity. The high-molecular weight derivative of camptothecins of the present invention can be formulated into a dosage form usually used such as injection, tablet, powder and the like and used. In formulation, pharmaceutically acceptable carriers usually used, for example, binders, lubricants, disintegration agents, solvents, excipients, solubilizers, dispersing agents, stabilizers, suspending agents, preservatives, soothing agents, dyes, aromas and the like can be used. In the case of an injection, a solvent is usually used. Mentioned as the solvent are, for example, water, physiological saline, 5% glucose or mannitol liquid, water-soluble organic solvents, for example, glycerol, ethanol, dimethylsulfoxide, N-methylpyrrolidone, polyethylene glycol, cremophore and the like, mixtures thereof, and mixtures of water and the above-mentioned water-soluble organic solvents, and the like.

The dosage of the high-molecular weight derivative of camptothecins of the present invention can be naturally altered depending on the sex, age, physiological conditions, pathologic conditions and the like of patient, and it is administered parenterally usually at a dose of 0.01 to 500 mg/m² (body surface area), preferably 0.1 to 250 mg/m² as an active component a day for an adult. Administration by injection is conducted intravenously, intraarterially, locally (tumor part) and the like.

EXAMPLES

The present invention will be illustrated further specifically by examples below, but is not limited to these examples.

Example 1

Synthesis of compound 1 (condensate of a block copolymer of methoxypolyethylene glycol having a molecular weight of approximately 12000 and polyglutamic acid having a polymerization number of approximately 28, with 7-ethyl-10-hydroxycamptothecin: general formula (I) in which $R_1$=Me, A=trimethylene group, d+e+f=approximately 28, t=approximately 273, $R_2$=Et, $R_3$=H, P=Ac)

A methoxypolyethylene glycol-polyglutamic acid block copolymer (210 mg) described in the following Reference Example 1 and 7-ethyl-10-hydroxycamptothecin (80 mg) produced in a method described in Japanese Patent Publication No. 62-47193 were dissolved in DMF (14 ml), to this was added DMAP (13.5 mg) and DIPC (0.116 ml), and the mixture was stirred for 20 hours at room temperature. To the reaction liquid, ethanol (40 ml) and diisopropyl ether (160 ml) were added and the mixture was stirred for 30 minutes at room temperature, then, the precipitate was filtrated, and washed with ethanol/diisopropyl ether (1/4 (v/v), 150 ml). The resultant precipitate was dissolved in acetonitrile/water (1/3 (v/v), 40 ml), then, passed through a column of an ion exchange resin (Dowex 50 ($H^+$), 5 ml), and eluted by acetonitrile/water (1/3 (v/v), 40 ml). From the resultant elution fraction, acetonitrile was distilled off under reduced pressure, then, freeze-dried to obtain compound 1 (270 mg). To a polyglutamic acid portion of compound 1, camptothecins and an isopropylaminocarbonylisopropylamino group are bonded. The content of camptothecins in the compound was determined based on absorbancy at 330 nm in a DMF solution to find a proportion of 25.4% (w/w). Regarding the content of an isopropylaminocarbonylisopropylamino group, the hydrogen nuclear magnetic resonance spectrum of a high-molecular weight derivative of camptothecins was measured in a deuterium oxide-acetonitrile-$d_3$ mixed solution containing sodium deuteroxide, and from the intensity ratio of the signals and the above-mentioned content of camptothecins, the content was calculated to find 3.0% (w/w). As a result, the ratio of d was 15.5% and the ratio of f was 48.4% based on d+e+f. Compound 1 obtained above was analyzed by high performance liquid chromatography (HPLC), and the content of free camptothecins was 0.3% or less.

Example 2

Synthesis of compound 2 (condensate of a block copolymer of mono-methoxypolyethylene glycol having a molecular weight of approximately 12000 and polyglutamic acid having a polymerization number of approximately 7, with 7-ethyl-10-hydroxycamptothecin: general formula (I) in which $R_1$=Me, A=trimethylene group, d+e+f=approximately 7, t=approximately 273, $R_2$=Et, $R_3$=H, P=Ac)

Methoxypolyethylene glycol-polyglutamic acid (797 mg) described in the following Reference Example 2 and 7-ethyl-10-hydroxycamptothecin (80 mg) produced in a method described in Japanese Patent Publication No. 62-47193 were dissolved in DMF (14 ml), to this was added DMAP (16.6 mg) and DIPC (0.142 ml), and the mixture was stirred for 20 hours at room temperature. To the reaction liquid, ethanol (40 ml) and diisopropyl ether (160 ml) were added and the mixture was stirred for 30 minutes at room temperature, then, the precipitate was filtrated, and washed with ethanol/diisopropyl ether (1/4 (v/v), 150 ml). The resultant precipitate was dissolved in acetonitrile/water (1/3 (v/v), 40 ml), then, passed through a column of an ion exchange resin (Dowex 50 ($H^+$), 5 ml), and eluted by acetonitrile/water (1/3 (v/v), 40 ml). From the resultant elution fraction, acetonitrile was distilled off under reduced pressure, then, freeze-dried to obtain compound 2 (818 mg). The content of camptothecins in the compound was determined based on absorbancy at 330 nm in a DMF solution to find a proportion of 9.6% (w/w). The content of an isopropylaminocarbonylisopropylamino group was measured by the same procedure as in Example 1 to find 1.5% (w/w). As a result, the ratio of d was 20.3% and the ratio of f was 47.2% based on d+e+f. Compound 2 obtained above was analyzed by HPLC, and the content of free camptothecins was 0.2% or less.

Example 3

Drug Release in the Absence of Hydrolytic Enzyme

The high-molecular weight derivative of camptothecins in Examples 1 and 2 were respectively dissolved in PBS (phosphate buffer saline; pH 7.1) and incubated at 37° C. 7-Ethyl-10-hydroxycamptothecin released from the high-molecular weight derivatives was separated and measured by HPLC. In comparison with a standard curve in this treatment, the amount of 7-ethyl-10-hydroxycamptothecin was calculated. This value was shown in FIG. 1 as a ratio based on the total drug amount measured from the drug content of a high-molecular weight prodrug. FIG. 1 shows that a drug is sustained-released from the high-molecular weight derivative of camptothecins of the present invention without depending on hydrolytic enzyme.

Example 4

Drug Release in the Presence of Mouse Plasma

Figure 2:
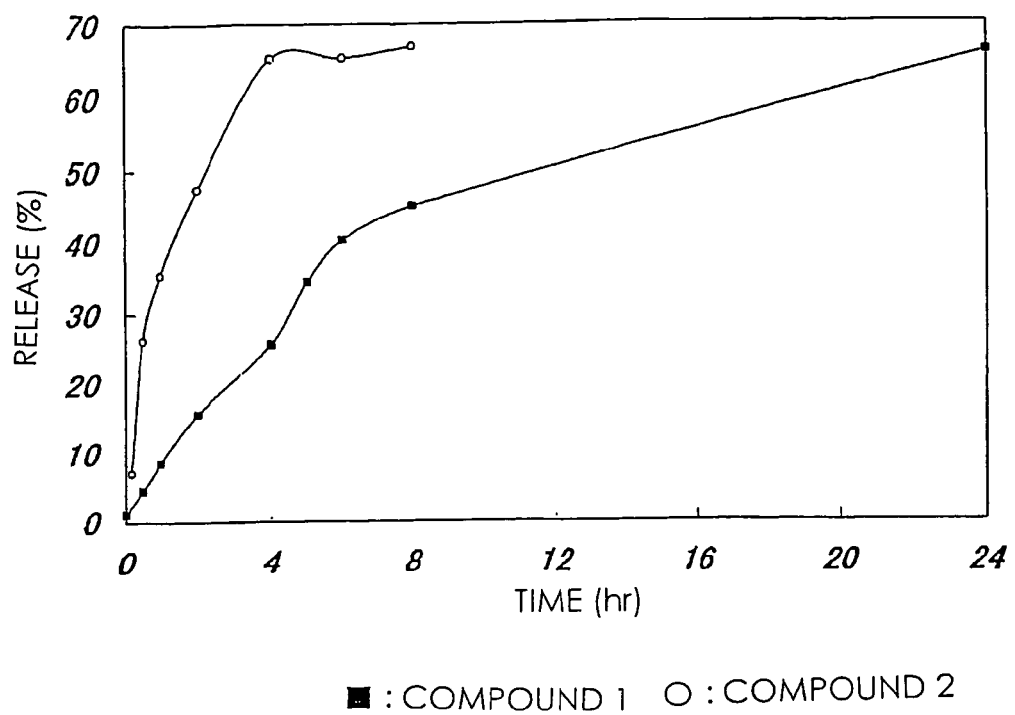
FIG. 2 is a curve diagram showing the release amount of drugs in the presence of mouse plasma in terms of ratio based on the total drug amount in Example 4. The abscissa represents time and the ordinate represents release amount.

The high-molecular weight derivative of camptothecins in Examples 1 and 2 were respectively dissolved in 5% glucose aqueous solution, then, mouse (male) plasma was added in 4-fold amount (v/v) of the 5% glucose aqueous solution, and incubated at 37° C. Then, the solution was removed with the lapse of time by 0.1 ml, and methanol/acetonitrile (1/1 (v/v), 0.4 ml) was added to conduct protein-removal treatment, and 7-ethyl-10-hydroxycamptothecin released from the high-molecular weight derivatives was separated and measured by HPLC. In comparison with a standard curve in this treatment, the amount of 7-ethyl-10-hydroxycamptothecin was calculated. This value was shown in FIG. 2 as a ratio based on the total drug amount measured from the drug content of a high-molecular weight prodrug. FIG. 2 shows that a drug is sustained-released from the high-molecular weight derivative of camptothecins of the present invention also in plasma.

Example 5

Antitumor Action

Mouse colon cancer Colon 26 tumor under successive cultivation under mouse skin was cut into blocks of approximately 2 mm square, and transplanted to under mouse skin using a trochar. 7 days after transplantation of the tumor, a high-molecular weight derivative of camptothecins of the present invention and CPT-11 as a control drug were dissolved respectively in 5% glucose aqueous solution, and administered intravenously once. After administration, the major axis (L mm) and minor axis (W mm) of the tumor were measured at an interval of 2 to 3 days using a caliper, and the volume of the tumor was calculated according to $(L \times W^2)/2$, and the relative tumor volume was determined from the volume at the day of administration initiation (Table 1). As an indication of toxicity, variation in body weight was also measured (Table 2). As a result, the high-molecular weight derivative of camptothecins of the present invention had little toxicity (body weight reduction), and showed reinforced antitumor effect as compared with CPT-11. The high-molecular weight derivative of camptothecins having larger drug content (compound 1) gave a higher antitumor effect with smaller administration amount, as compared with the high-molecular weight derivative of camptothecins having smaller drug content (compound 2).

TABLE 1

|  | Dose | Days after administration | | | | | | |
|---|---|---|---|---|---|---|---|---|
|  |  | 0 | 2 | 5 | 7 | 9 | 12 | 14 |
| No-treatment group |  | 1.0 | 2.5 | 8.1 | 12.8 | 14.5 | 15.5 | 14.3 |
| Compound 1 | 45.0 mg/kg | 1.0 | 0.9 | 0.4 | 0.3 | 0.5 | 0.9 | 2.6 |
|  | 22.5 mg/kg | 1.0 | 0.8 | 0.6 | 1.0 | 1.8 | 7.2 | 8.5 |
| Compound 2 | 180.0 mg/kg | 1.0 | 0.8 | 0.9 | 1.5 | 3.8 | 9.8 | 13.8 |
|  | 90.0 mg/kg | 1.0 | 1.0 | 1.4 | 3.5 | 8.8 | 16.5 | 17.7 |
| CPT-11 | 26.1 mg/kg | 1.0 | 1.8 | 8.4 | 10.3 | 12.8 | 33.2 | 34.1 |

TABLE 2

|  | Dose | Days after administration | | | | | | |
|---|---|---|---|---|---|---|---|---|
|  |  | 0 | 2 | 5 | 7 | 9 | 12 | 14 |
| No-treatment group |  | 1.0 | 1.01 | 1.02 | 0.97 | 0.89 | 0.80 | 0.81 |
| Compound 1 | 45.0 mg/kg | 1.0 | 0.94 | 0.91 | 0.97 | 1.01 | 1.03 | 1.04 |
|  | 22.5 mg/kg | 1.0 | 0.98 | 1.02 | 1.01 | 1.06 | 1.03 | 0.96 |
| Compound 2 | 180.0 mg/kg | 1.0 | 0.91 | 0.99 | 0.99 | 1.04 | 0.94 | 0.94 |
|  | 90.0 mg/kg | 1.0 | 0.96 | 1.00 | 1.01 | 1.01 | 0.90 | 0.83 |
| CPT-11 | 26.1 mg/kg | 1.0 | 1.00 | 1.01 | 0.90 | 0.79 | 0.88 | 0.87 |

Reference Example 1

Synthesis of N-acetylated Compound of a Block Copolymer of Mono-Methoxypolyethylene Glycol Having a Molecular Weight of Approximately 12000 and Polyglutamic Acid Having a Polymerization Number of Approximately 28

Polyethylene glycol (SUNBRIGHT MEPA-12T, manufactured by NOF Corp., average molecular weight 12000, 1.0 g) having a methoxy group at one end and a 3-aminopropyl group at another end was dissolved in DMSO (20 ml), then, γ-benzyl L-glutamate N-carboxy anhydride (0.77 g) was added to this and the mixture was stirred for 20 hours at 35° C. To the reaction liquid was added ethanol (80 ml) and diisopropyl ether (320 ml) and the mixture was stirred for 90 minutes at room temperature, then, the precipitate was filtrated and washed with ethanol/diisopropyl ether (1/4 (v/v), 100 ml). The resultant precipitate was dissolved in DMF (20 ml), to this was added acetic anhydride (0.4 ml) and the mixture was stirred for 15 hours at room temperature. To the reaction liquid was added ethanol (80 ml) and diisopropyl ether (320 ml) and the mixture was stirred for 90 minutes at room temperature, then, the precipitate was filtrated and washed with ethanol/diisopropyl ether (1/4 (v/v), 100 ml), to obtain 1.56 g of polymer. The resultant polymer was dissolved in DMF (47 ml), then, 5% palladium-carbon (780 mg) was added and hydrogenolysis was conducted at 35° C. for 3 hours. To the reaction liquid was added methanol (90 ml) and celite (8 g) and the mixture was stirred for 2 hours, then, 5% palladium-carbon was filtrated off. Methanol was distilled off under reduced pressure, then, ethanol (90 ml) and diisopropyl ether (360 ml) were added, and the mixture was stirred for 90 minutes at room temperature. The precipitate was filtrated and washed with ethanol/diisopropyl ether (1/4 (v/v), 100 ml), then, dissolved in 10% saline (100 ml). pH of the dissolved liquid was controlled to 10.0 with a 1 N sodium hydroxide aqueous solution, then, the liquid was purified by distribution adsorption resin column chromatography, subsequently, ion exchange resin column chromatography, and the eluted solution was concentrated under reduced pressure, then, freeze-dried to obtain an intended compound (1.18 g). The polymerization number of glutamic acid in one molecule of this compound based on the titration value using 0.02 N sodium hydroxide was approximately 28.

Reference Example 2

Synthesis of N-Acetylated Compound of Block Copolymer of Mono-Methoxypolyethylene Glycol Having a Molecular Weight of Approximately 12000 and Polyglutamic Acid Having a Polymerization Number of Approximately 7

Polyethylene glycol (SUNBRIGHT MEPA-12T, manufactured by NOF Corp., average molecular weight 12000, 2.0 g) having a methoxy group at one end and a 3-aminopropyl group at another end was dissolved in DMSO (40 ml), then, γ-benzyl L-glutamate N-carboxy anhydride (0.40 g) was added to this and the mixture was stirred for 20 hours at 35° C. To the reaction liquid was added ethanol (160 ml) and diisopropyl ether (640 ml) and the mixture was stirred for 90 minutes at room temperature, then, the precipitate was filtrated and washed with ethanol/diisopropyl ether (1/4 (v/v), 150 ml). The resultant precipitate was dissolved in DMF (40 ml), to this was added acetic anhydride (0.8 ml) and the mixture was stirred for 15 hours at room temperature. To the reaction liquid was added ethanol (160 ml) and diisopropyl ether (640 ml) and the mixture was stirred for 90 minutes at room temperature, then, the precipitate was filtrated and washed with ethanol/diisopropyl ether (1/4 (v/v), 150 ml), to obtain 2.12 g of polymer. The resultant polymer was dissolved in DMF (64 ml), then, 5% palladium-carbon (1.06 g) was added and hydrogenolysis was conducted at 35° C. for 3 hours. To the reaction liquid was added methanol (130 ml) and celite (14 g) and the mixture was stirred for 2 hours, then, 5% palladium-carbon was filtrated off. Methanol was distilled off under reduced pressure, then, ethanol (130 ml) and diisopropyl ether (520 ml) were added, and the mixture was stirred for 90 minutes at room temperature. The precipitate was filtrated and washed with ethanol/diisopropyl ether (1/4 (v/v), 160 ml), then, dissolved in 10% saline (160 ml). pH of the dissolved liquid was controlled to 10.0 with a 1 N sodium hydroxide aqueous solution, then, the liquid was purified by distribution adsorption resin column chromatography, subsequently, ion exchange resin column chromatography, and the eluted solution was concentrated under reduced pressure, then, freeze-dried to obtain an intended compound (1.56 g). The polymerization number of glutamic acid in one molecule of this compound based on the titration value using 0.02 N sodium hydroxide was approximately 7.

INDUSTRIAL APPLICABILITY

The high-molecular weight derivative of camptothecins of the present invention is a high-molecular weight derivative showing sustained release even in an organism and excellent in treatment effect because of bonding of camptothecins by a phenylester bond which is easily decomposed chemically. Further, a high-molecular weight derivative forming micelle is expected to show a drug effect selectively at disease parts and to provide little side effect. Furthermore, since release of physiologically active substances without depending on enzyme is possible, little influence by differences in individual patients is expected in respect of treatment effect.

What is claimed is:

1. A high-molecular weight derivative of camptothecins of the general formula (I):

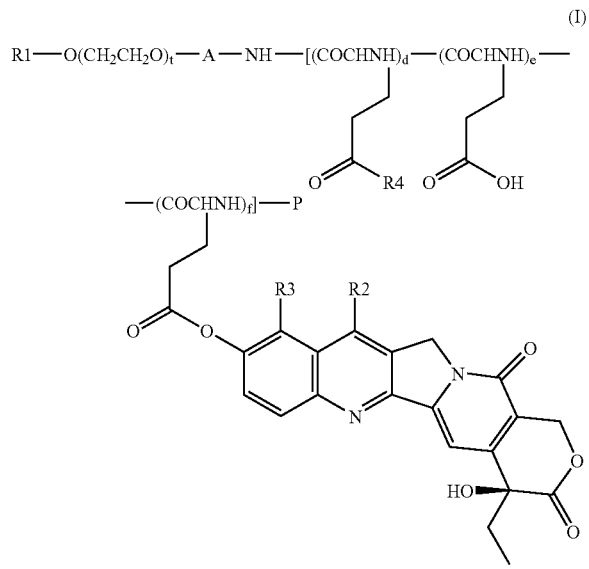

[wherein, R1 represents a hydrogen atom or a (C1 to C6) alkyl group optionally having a substituent, t represents an integer of 5 to 11500, A represents a bonding group, d+e+f represents an integer of 3 to 200, R2 represents a hydrogen atom or a (C1 to C6) alkyl group optionally having a substituent or a silyl group optionally having a substituent, R3 represents a hydrogen atom or a (C1 to C6) alkyl group optionally having a substituent, R4 may be the same or different and represents a (C1 to C20) alkoxyl group optionally having a substituent, a (C1 to C20) alkylamino group optionally having a substituent, a di(C1 to C20) alkylamino group optionally having a substituent or a (C1 to C20) alkylaminocarbonyl (C1 to C20) alkylamino group optionally having a substituent, and P represents a hydrogen atom, a (C1 to C6) acyl group or a (C1 to C6) alkoxycarbonyl group.].

2. The high-molecular weight derivative of camptothecins according to claim 1, wherein R1 is a (C1 to C4) alkyl group optionally having a substituent, t is an integer of 100 to 300, A is a (C2 to C6) alkylene group, d+e+f is an integer of 6 to 60, the ratio of d is 0 to 60%, the ratio of e is 0 to 60% and the ratio of f is 1 to 100% based on d+e+f, R2 is a hydrogen atom or a (C1 to C4) alkyl group optionally having a substituent, R3 is a hydrogen atom or a (C1 to C4) alkyl group having no substituent, R4 may be the same or different and is a (C1 to C8) alkoxyl group optionally having a substituent, (C1 to C8) alkylamino group optionally having a substituent, di (C1 to C8) alkylamino group optionally having a substituent or (C1 to C8) alkylaminocarbonyl (C1 to C8) alkylamino group optionally having a substituent, and P is a (C2 to C4) acyl group.

3. The high-molecular weight derivative of camptothecins according to claim 2, wherein R1 is a methyl group, A is a trimethylene group, R2 is a hydrogen atom, R3 is a dimethylaminomethyl group, R4 is an isopropylaminocarbonylisopropylamino group, and P is an acetyl group.

4. The high-molecular weight derivative of camptothecins according to claim 2, wherein R1 is a methyl group, A is a trimethylene group, R2 is an ethyl group, R3 is a hydrogen atom, R4 is an isopropylaminocarbonylisopropylamino group, and P is an acetyl group.

5. A method of producing the high-molecular weight derivative of camptothecins according to any one of claims 1 to 4, comprising combining a carboxylic acid group of a copolymer of polyethylene glycol and a polymer having a carboxylic acid group at the side chain, with a phenolic hydroxyl group of phenolic camptothecins via an ester bond, using a condensing agent.

6. An anticancer agent comprising the high-molecular weight derivative of camptothecins according to any one of claims 1 to 5.

* * * * *